United States Patent
Huang et al.

(10) Patent No.: US 8,268,228 B2
(45) Date of Patent: Sep. 18, 2012

(54) METHOD OF FABRICATING STENTS FROM BLOW MOLDED TUBING

(75) Inventors: Bin Huang, Pleasanton, CA (US); David C. Gale, San Jose, CA (US); Vincent J. Gueriguian, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 140 days.

(21) Appl. No.: 12/001,777

(22) Filed: Dec. 11, 2007

(65) Prior Publication Data
US 2009/0146348 A1 Jun. 11, 2009

(51) Int. Cl.
*B29C 49/00* (2006.01)
(52) U.S. Cl. .......... 264/535; 264/523; 264/564
(58) Field of Classification Search .......... 264/40.6, 264/523, 535
See application file for complete search history.

(56) References Cited

U.S. PATENT DOCUMENTS

| | | |
|---|---|---|
| 3,636,956 A | 1/1972 | Schneider |
| 4,547,416 A | 10/1985 | Reed et al. |
| 4,698,196 A | 10/1987 | Fabian et al. |
| 4,702,884 A | 10/1987 | Goldstein |
| 4,957,687 A | 9/1990 | Akman et al. |
| 4,987,025 A | 1/1991 | Shiraki et al. |
| 5,087,394 A | 2/1992 | Keith |
| 5,108,416 A | 4/1992 | Ryan et al. |
| 5,116,365 A | 5/1992 | Hillstead |
| 5,147,302 A | 9/1992 | Euteneuer et al. |
| 5,500,013 A | 3/1996 | Buscemi et al. |
| 5,628,786 A | 5/1997 | Banas et al. |
| 5,670,161 A | 9/1997 | Healy et al. |
| 5,891,386 A | 4/1999 | Deitermann et al. |
| 6,572,813 B1 | 6/2003 | Zhang et al. |
| 6,626,939 B1 | 9/2003 | Burnside et al. |
| 6,645,422 B2 | 11/2003 | Jung et al. |
| 7,066,952 B2 | 6/2006 | Igaki |
| 7,070,615 B1 | 7/2006 | Igaki |
| 7,083,639 B2 | 8/2006 | Guinan et al. |
| 7,128,868 B2 | 10/2006 | Eidenschink |
| 2001/0014821 A1 | 8/2001 | Juman et al. |
| 2002/0077592 A1 | 6/2002 | Barry |
| 2002/0138133 A1 | 9/2002 | Lenz et al. |
| 2002/0151965 A1 | 10/2002 | Roth |
| 2003/0028241 A1 | 2/2003 | Stinson |
| 2003/0028246 A1 | 2/2003 | Palmaz et al. |

(Continued)

FOREIGN PATENT DOCUMENTS

EP 0 583 170 2/1994

(Continued)

OTHER PUBLICATIONS

John C. Middleton and Arthur J. Tipton; Synthetic Biodegradable Polymers as Medical Devices; Mar. 1998; Medical Device and Diagnostic Industry; website: http://www.mddionline.com/article/synthetic-biodegradable-polymers-medical-devices.*

(Continued)

*Primary Examiner* — Yogendra Gupta
*Assistant Examiner* — Ninh Le
(74) *Attorney, Agent, or Firm* — Squire Sanders (US) LLP

(57) ABSTRACT

Methods to expand polymer tubing with desirable or optimum morphology and mechanical properties for stent manufacture and fabrication of a stent therefrom are disclosed.

19 Claims, 7 Drawing Sheets

U.S. PATENT DOCUMENTS

| | | | |
|---|---|---|---|
| 2003/0050687 A1* | 3/2003 | Schwade et al. | 623/1.15 |
| 2003/0055488 A1 | 3/2003 | Igaki | |
| 2003/0083732 A1 | 5/2003 | Stinson | |
| 2003/0187158 A1 | 10/2003 | Preuschen et al. | |
| 2003/0208254 A1 | 11/2003 | Shortt | |
| 2003/0226833 A1 | 12/2003 | Shapovalov et al. | |
| 2004/0000361 A1 | 1/2004 | Trozera | |
| 2004/0098090 A1 | 5/2004 | Williams et al. | |
| 2005/0004663 A1 | 1/2005 | Llanos et al. | |
| 2005/0137678 A1 | 6/2005 | Varma | |
| 2005/0177130 A1 | 8/2005 | Konstantino et al. | |
| 2005/0187615 A1 | 8/2005 | Williams et al. | |
| 2005/0196485 A1 | 9/2005 | Cass et al. | |
| 2006/0020330 A1 | 1/2006 | Huang et al. | |
| 2006/0076708 A1 | 4/2006 | Huang et al. | |
| 2006/0211952 A1 | 9/2006 | Kennedy | |
| 2006/0224226 A1 | 10/2006 | Huang et al. | |
| 2007/0253996 A1 | 11/2007 | Bin et al. | |
| 2007/0253999 A1 | 11/2007 | Huang et al. | |
| 2007/0282431 A1* | 12/2007 | Gale et al. | 623/1.38 |
| 2007/0282433 A1 | 12/2007 | Limon et al. | |
| 2007/0283552 A1 | 12/2007 | Gale et al. | |
| 2007/0290412 A1 | 12/2007 | Capek et al. | |
| 2007/0293938 A1 | 12/2007 | Gale et al. | |
| 2008/0001333 A1 | 1/2008 | Kleine et al. | |
| 2009/0001633 A1 | 1/2009 | Limon et al. | |
| 2009/0005860 A1 | 1/2009 | Huang et al. | |
| 2009/0012598 A1 | 1/2009 | Abbate et al. | |
| 2009/0146348 A1 | 6/2009 | Huang et al. | |

FOREIGN PATENT DOCUMENTS

| | | |
|---|---|---|
| EP | 1 800 628 | 6/2007 |
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 03/034940 | 5/2003 |
| WO | WO 2004/067262 | 8/2004 |
| WO | WO 2006/014747 | 2/2006 |

OTHER PUBLICATIONS

U.S. Appl. No. 10/882,136, filed Jun. 29, 2004, Abbate et al.
U.S. Appl. No. 10/881,554, filed Jun. 29, 2004, Abbate et al.
U.S. Appl. No. 10/956,910, filed Sep. 30, 2004, Huang et al.
U.S. Appl. No. 10/956,911, filed Sep. 30, 2004, Durcan.
U.S. Appl. No. 10/956,759, filed Sep. 30, 2004, Durcan.
U.S. Appl. No. 11/809,011, filed May 30, 2007, Gueriguian et al.
U.S. Appl. No. 11/823,954, filed Jun. 29, 2007, Huang et al.
U.S. Appl. No. 11/771,967, filed Jun. 29, 2007, Limon et al.
International Search Report for PCT/US2008/086054, mailed Apr. 24, 2009, 7 pgs.
Answers.com blow molding; retrieved from www.answers.com/blow%20molding#Stretch_blow_molding, Jun. 26, 2009, 11 pgs.
www.engineeringtoolbox.com/thermal/conductivity/d_429.html., Jun. 26, 2009, 4 pgs.

* cited by examiner

METHOD OF FABRICATING STENTS FROM BLOW MOLDED TUBING

BACKGROUND OF THE INVENTION

1. Field of the Invention

This invention relates to methods of blow molding polymeric tubing for stent manufacturing.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodible materials such as bioabsorbable polymers should be configured to completely erode only after the clinical need for them has ended.

There are several characteristics that are important for implantable medical devices, such as stents, including high radial strength and good fracture toughness. Some crystalline or semi-crystalline polymers that may be suitable for use in implantable medical devices have potential shortcomings with respect to some of these characteristics, in particular, fracture toughness.

SUMMARY OF THE INVENTION

Various embodiments of the present invention include a method for fabricating stent comprising: radially deforming a polymer tube for use in fabrication of a stent from the deformed tube, wherein the radial deformation propagates along the tube axis as the tube is heated along the axis, the polymer tube having an internal tube pressure higher than ambient; controlling the propagation rate or the radial deformation rate to provide a selected fracture resistance of a stent fabricated from the tube; and fabricating the stent from the deformed tube.

Further embodiments of the present invention include a method for fabricating a stent comprising: radially deforming a polymer tube for use in fabrication of a stent from the deformed tube, wherein the radial deformation propagates along the tube axis as the tube is heated along the axis, the polymer tube having an internal tube pressure higher than ambient; controlling a temperature of the polymer tube to provide a selected fracture resistance of the stent fabricated from the tube; and fabricating the stent from the deformed tube.

Additional embodiments of the present invention include a method for fabricating a stent comprising: increasing an internal pressure of a tube to a deformation pressure; translating a heat source along an axis of the polymer tube to heat the tube to a deformation temperature; allowing the tube to radially expand as the heat source translates along the axis of the polymer tube, wherein the heating of the tube and the increase in pressure allow the tube to radially expand; and controlling one or more process parameters to provide a selected fracture resistance a stent fabricated from the tube, wherein the process parameters are selected from the group consisting of the deformation pressure, the translation rate of the heat source, the deformation temperature; and fabricating the stent from the deformed tube.

Other embodiments of the present invention include a method for fabricating a stent comprising: determining one or more process parameters of a radial deformation process of a tube to provide a selected fracture resistance of a stent fabricated from the tube, the radial deformation process comprising: increasing an internal pressure of a tube to a deformation pressure; translating a heat source along an axis of the polymer tube to heat the tube to a deformation temperature; allowing the tube to radially expand as the heat source translates along the axis of the polymer tube, wherein the heating of the tube and the increase in pressure allow the tube to radially expand, wherein the process parameters are selected from the group consisting of the deformation pressure, the translation rate of the heat source, the deformation temperature; and fabricating the stent from the deformed tube.

Further embodiments of the present invention include a method for fabricating a stent comprising: increasing an internal pressure of a polylactide tube to between 120 psi and 130 psi; translating a heat source along an axis of the polymer tube at a translation rate between 0.5 and 0.7 mm/s to heat the tube to between 190° F. and 210° F.; allowing the tube to radially expand as the heat source translates along the axis of the polymer tube, wherein the heating of the tube and the increase in pressure allow the tube to radially expand; and fabricating the stent from the deformed tube.

DETAILED DESCRIPTION OF THE INVENTION

Figure 1:
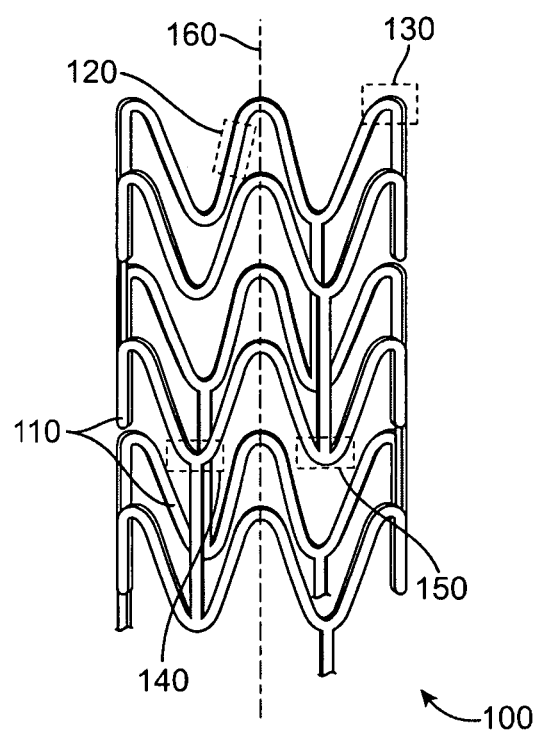
FIG. 1 depicts a stent.

The various embodiments of the present invention relate to methods of fabricating a polymeric stent that have good or optimal toughness and selected mechanical properties along the axial direction or circumferential direction of the stent, or both. The present invention can be applied to devices including, but is not limited to, self-expandable stents, balloon-expandable stents, stent-grafts, and grafts (e.g., aortic grafts).

For the purposes of the present invention, the following terms and definitions apply:

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that results from the applied force. For example, a material has both a tensile and a compressive modulus.

"Stress at peak" is the maximum tensile stress which a material will withstand prior to fracture. Stress at break can also be referred to as the tensile strength. The stress at break is calculated from the maximum load applied during a test divided by the original cross-sectional area.

"Stress at break" is the tensile stress of a material at fracture.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

A stent can have a scaffolding or a substrate that includes a pattern of a plurality of interconnecting structural elements or struts. FIG. 1 depicts an example of a view of a stent 100. Stent 100 has a cylindrical shape with an axis 160 and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Figure 2:
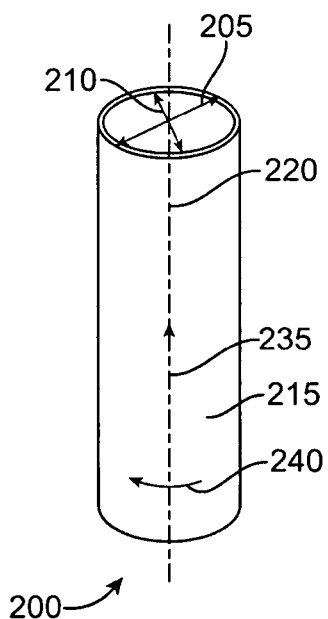
FIG. 2 depicts a tube.

A stent such as stent 100 may be fabricated from a polymeric tube or a sheet by rolling and bonding the sheet to form a tube. For example, FIG. 2 depicts a tube 200. Tube 200 is cylindrically-shaped with an outside diameter 205 and an inside diameter 210. FIG. 2 also depicts an outside surface 215 and a cylindrical axis 220 of tube 200. In some embodiments, the diameter of the polymer tube prior to fabrication of an implantable medical device may be between about 0.2 mm and about 5.0 mm, or more narrowly between about 1 mm and about 3 mm. Polymeric tubes may be formed by various types of methods, including, but not limited to extrusion or injection molding.

A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

The pattern of stent 100 in FIG. 1 varies throughout its structure to allow radial expansion and compression and longitudinal flexure. A pattern may include portions of struts that are straight or relatively straight, an example being a portion 120. In addition, patterns may include bending elements 130, 140, and 150.

Bending elements bend inward when a stent is crimped to allow radial compression. Bending elements also bend outward when a stent is expanded to allow for radial expansion. After deployment, a stent is under static and cyclic compressive loads from the vessel walls. Thus, bending elements are subjected to deformation during use. "Use" includes, but is not limited to, manufacturing, assembling (e.g., crimping stent on a catheter), delivery of stent into and through a bodily lumen to a treatment site, and deployment of stent at a treatment site, and treatment after deployment.

Additionally, stent 100 is subjected to flexure along axis 160 when it is maneuvered through a tortuous vascular path during delivery. Stent 100 is also subjected to flexure when it has to conform to a deployment site that may not be linear.

There are several mechanical properties that are important for a stent. These include high radial strength, adequate toughness, low recoil, and resistance to physical aging. A stent must have adequate strength, particularly, in the radial direction to withstand structural loads, namely radial compressive forces, imposed on the stent as it supports the walls of a vessel. Radial strength is associated with strength of the stent around the circumferential direction of the stent. In addition, the stent must possess sufficient toughness so that the stent exhibits sufficient flexibility to allow for crimping, expansion, and flexure. A stent should have sufficient toughness so that it is resistant to crack formation, particularly, in high strain regions. Recoil refers to the retraction of a stent radially inward from its deployed diameter.

A stent can be made in whole or in part of a biodegradable polymer. A biodegradable stent can be configured erode away from an implant site when it is no longer needed. A biodegradable stent allows further surgery or intervention, if necessary, on a treated vessel and reduces the likelihood of late stent thrombosis, a condition in which clots form on the surface of the stent months or years after deployment. Some crystalline or semi-crystalline biodegradable polymers that are glassy or have a glass transition temperature (Tg) above body temperature are particularly attractive as stent materials due to their strength and stiffness at physiological conditions. Such glassy polymers can be absorbed through chemical degradation, such as hydrolysis. Physiological conditions refer to conditions that an implant is exposed to within a human body. Physiological conditions include, but are not limited to, human body temperature, approximately 37° C.

However, the mechanical properties of such polymers may require improvement to be suitable as stent materials. For example, the struts of stent may have to be undesirably large to have radial strength sufficient to support the walls of a vessel. Therefore, the strength of such polymers may need improvement. Additionally, the toughness of such polymers can be lower than desired, in particular, for use in stent applications. For example, polymers such as poly(L-lactide) (PLLA) are stiff and strong, but tend to be brittle under physiological conditions. These polymers can exhibit a brittle fracture mechanism at physiological conditions in which there is little or no plastic deformation prior to failure. A stent fabricated from such polymers can have insufficient toughness for the range of use of a stent. As a result, cracks, particularly in high strain regions, can be induced which can result in mechanical failure of the stent.

Furthermore, recoil can result from creep and stress relaxation which result from relaxation or rearrangement of polymer chains. Creep refers to the gradual deformation that occurs in a polymeric construct subjected to an applied load. Stress relaxation occurs when deformation (or strain) is constant and is manifested by a reduction in the force (stress) required to maintain a constant deformation Physical aging can also be a problem with such semicrystalline polymers. Physical aging, as used herein, refers to densification in the amorphous regions of a semi-crystalline polymer. Densification is the increase in density of a material or region of a material and results from reordering of polymer chains. Densification tends to decrease the fracture toughness of a polymer.

In general, the mechanical properties of a polymer depend upon its morphology or microstructure. Various embodiments of the present invention include processing a polymeric construct that is a precursor to a stent to obtain desirable or selected mechanical properties of the stent. Such desirable or selected mechanical properties can correspond to a particular structure or morphology. Embodiments of the present invention include adjusting the processing conditions to obtain selected or desirable properties.

Morphology includes, but is not limited to, crystallinity, molecular orientation of polymer chains, and crystal size. A polymer may be completely amorphous, partially crystalline, or almost completely crystalline. A partially crystalline polymer includes crystalline regions separated by amorphous regions. The degree of crystallinity is the sum of all the crystalline regions. Molecular orientation refers to the relative orientation of polymer chains along a longitudinal or covalent axis of the polymer chains. The orientation can refer to both the orientation of polymer chains the crystalline regions and the amorphous regions.

The relationship between the morphology and mechanical properties can be of use in alleviating some of the shortcomings of the semi-crystalline polymers mentioned above. In general, the modulus of a polymer increases as crystallinity increases. As mentioned above, a semi-crystalline polymer with a high degree of crystallinity can be brittle and is susceptible to cracking. An amorphous polymer may be more flexible or ductile, but may have insufficient radial strength. Additionally, the size of crystalline regions in a polymer can affect mechanical properties. It is believed that decreasing the size of crystalline regions or domains while maintaining a degree of crystallinity in a polymer increases the fracture toughness of the polymer.

Furthermore, the strength and toughness of a polymer can be affected by the orientation of polymer chains. The toughness of a semi-crystalline polymer can be increased by inducing orientation of polymer chains in both the crystalline and amorphous regions. In addition, the strength of the polymer is also increased along the direction of preferred orientation.

It is believed that crystalline domains can act as net points to tie polymer chains in the amorphous regions between the domains. Smaller domains at a given degree of crystallinity result in a greater number of domains and tie molecules, resulting in increased toughness. The strength and toughness of the amorphous regions can be further be increased by inducing orientation in the amorphous regions. It is expected that a higher number of net points and tie molecules with induced orientation can lead to higher strength and fracture toughness.

Certain embodiments of the present invention include processing a stent precursor construct, such as a polymer tube, to modify the morphology of the polymer in the construct so that the construct has desired or selected properties. It is well known by those skilled in the art that the mechanical properties of a polymer can be modified by applying stress to a polymer. James L. White and Joseph E. Spruiell, Polymer and Engineering Science, 1981, Vol. 21, No. 13. The application of stress can induce molecular orientation along the direction of stress which can modify mechanical properties along the direction of applied stress. Induced orientation in constructs such as polymer tubes can be particularly useful since tubes formed by extrusion tend to possess no or substantially no polymer chain alignment in the circumferential direction. A tube made from injection molding has a relatively low degree of polymer chain alignment in both the axial and circumferential directions.

In certain embodiments, the processing of the stent precursor construct can include deformation of a polymer tube radially, axially, or both to obtain selected or desirable mechanical properties. The processing can modify structural or morphological characteristics of the polymeric construct including crystallinity, crystal size, and molecular orientation. The processing can include radially deforming a polymer tube through application of an outwardly directed radial force. The radial force can be from an internal pressure of a fluid in the tube that is above ambient pressure. Ambient pressure corresponds to the pressure outside of the tube which is typically at or near atmospheric pressure.

Furthermore, the deformation can be facilitated by heating the tube prior to the deformation. Additionally, the tube can also be heated prior to and during the deformation of the tube. In some embodiments, the tube can be heated to a temperature above the Tg of the polymer of the tube.

In further embodiments, the polymeric tube can be axially deformed or stretched. The tube can be axially deformed by applying a tensile force at one end with the other end fixed or applying a tensile force at both ends. The temperature of the tube can be increased to a deformation temperature prior to the deformation of the tube and maintained at the deformation temperature during deformation. The deformation temperature may be in a range at or slightly below the Tg of the polymer of the tube to the melting temperature of the polymer of the tube. "Slightly below" the Tg can refer to temperatures of 5% below the Tg to the Tg of the polymer. The temperature of the tube can also be increased at a constant or nonlinear rate during deformation.

The degree of radial expansion, and thus induced radial orientation and strength, of a tube can be quantified by a radial expansion (RE) ratio:

$$\frac{\text{Inside Diameter of Expanded Tube}}{\text{Original Inside Diameter of Tube}}$$

The RE ratio can also be expressed as a percent expansion:

% Radial expansion=(RE ratio−1)×100%

Similarly, the degree of axial extension, and thus induced axial orientation and strength, may be quantified by an axial extension (AE) ratio:

$$\frac{\text{Length of Extended Tube}}{\text{Original Length of Tube}}$$

The AE ratio can also be expressed as a percent expansion:

% Axial expansion=(AE ratio−1)×100%

In further embodiments, the deformed tube can be heat set or annealed while the tube is maintained in the deformed state. In such embodiments, the internal pressure in the tube or the axial tension can be at levels that maintain the tube in the deformed state. The deformed tube can also be maintained at the deformation temperature or at a temperature above or below the deformation temperature. The heat setting or annealing can release internal stresses in the polymer. In addition, the heat setting or annealing allows crystallization to continue resulting in further increasing of the crystallinity. During the heat setting or annealing, the polymer chains are allowed to rearrange to approach an equilibrated configuration, relieving internal stresses.

Additionally, the deformed tube may then be cooled. The tube can be cooled slowly from above Tg to below Tg. Alternatively, the tube can be cooled quickly or quenched below Tg to an ambient temperature. The tube can be maintained at the deformed diameter during cooling.

In certain embodiments of the present invention, a polymeric tube may be deformed by blow molding. A balloon blowing apparatus may be adapted to radially deform a polymer tube. In blow molding, a tube can be deformed radially by conveying a fluid into the tube which increases the internal pressure in the tube. The polymer tube may be deformed axially by applying a tensile force by a tension source at one end while holding the other end stationary. Alternatively, a tensile force may be applied at both ends of the tube. The tube may be axially extended before, during, and/or after radial expansion.

In some embodiments, blow molding may include first positioning a tube in a cylindrical member or mold. The mold controls the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial deformation by limiting deformation of the inside diameter of the tube as an alternative to or in combination with using the mold.

As indicated above, the temperature of the tube can be heated to temperatures above the Tg of the polymer during deformation. The polymer tube may also be heated prior to, during, and subsequent to the deformation. In some embodiments, the tube may be heated by translating a heating source along the cylindrical axis of the tube. As the heat source translates and heats the tube, the radial deformation propagates along the axis of the tube. In other embodiments, in addition to the heat source, the tube may be heated by the mold or the fluid conveyed into the tube to expand the tube. The mold may be heated, for example, by heating elements on, in, and/or adjacent to the mold.

Certain embodiments may include first sealing, blocking, or closing a polymer tube at a distal end. The end may be open in subsequent manufacturing steps. The fluid, (conventionally a gas such as air, nitrogen, oxygen, argon, etc.) may then be conveyed into a proximal end of the polymer tube to increase the pressure in the tube. The pressure of the fluid in the tube may radially expand the tube.

Additionally, the pressure inside the tube, the tension along the cylindrical axis of the tube, and the temperature of the tube may be maintained above ambient levels for a period of time to allow the polymer tube to be heat set. Heat setting may include maintaining a tube at a temperature greater than or equal to the Tg of the polymer and less than the Tm of the polymer for a selected period to time. The selected period of time may be between about one minute and about two hours, or more narrowly, between about two minutes and about ten minutes. The polymer tube may then be cooled to below its Tg either before or after decreasing the pressure and/or decreasing tension. Cooling the tube helps insure that the tube maintains the proper shape, size, and length following its formation. Upon cooling, the deformed tube retains the length and shape imposed by an inner surface of the mold.

Figure 3A:
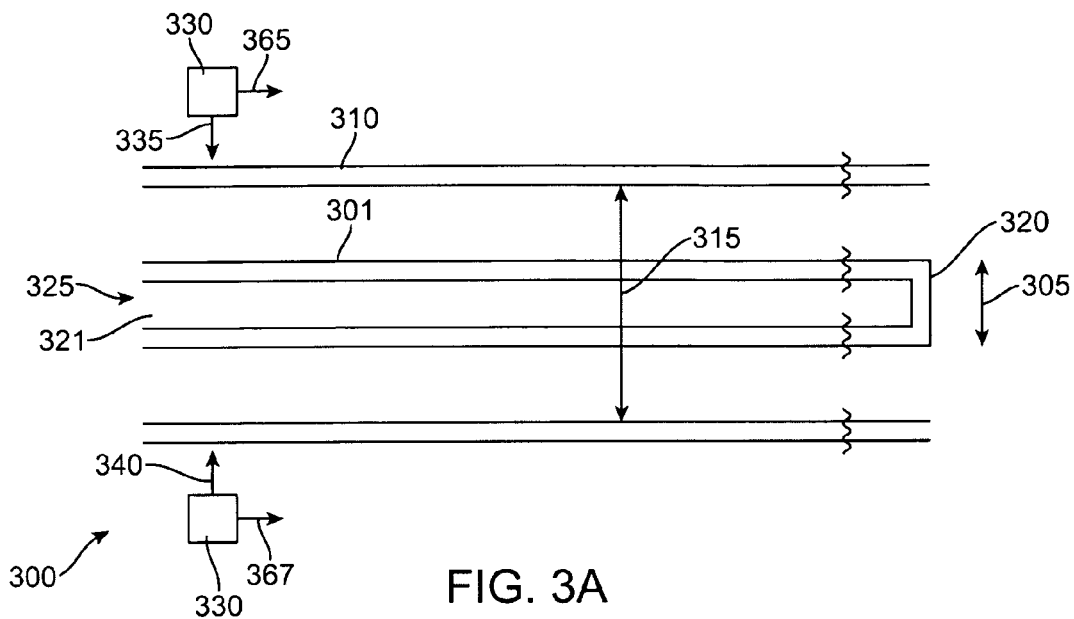
FIGS. 3A-3C depict blow molding of a polymeric tube.
Figure 3B:
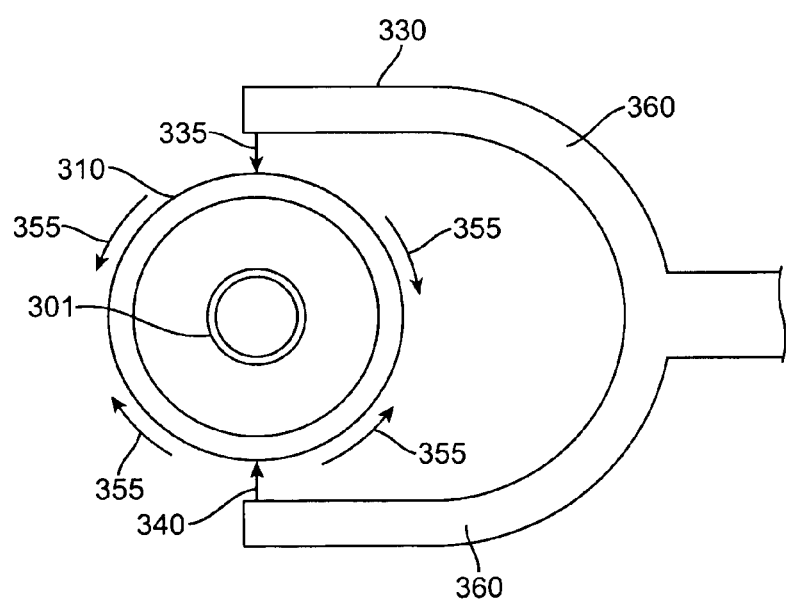
Figure 3C:
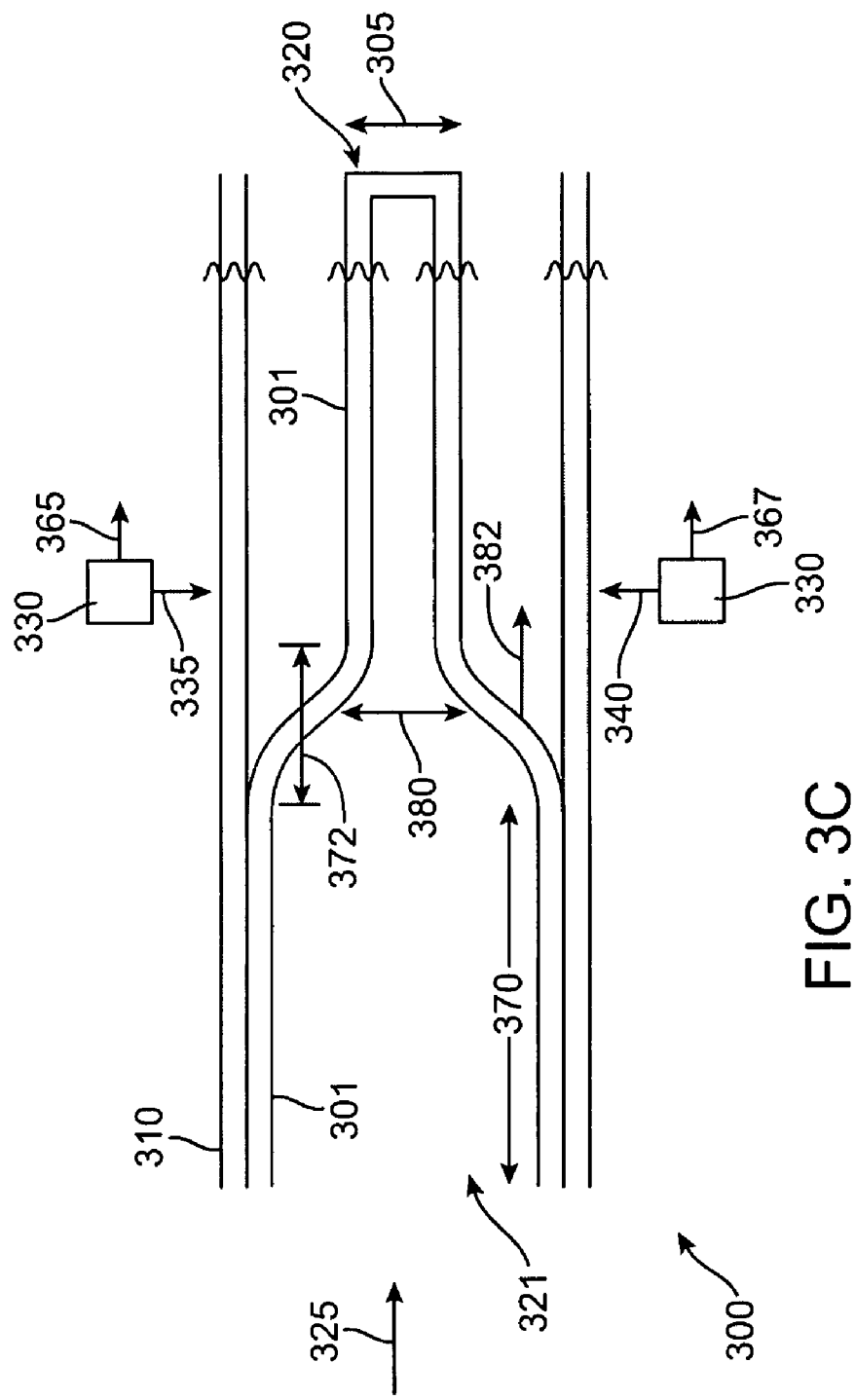

FIGS. 3A-C depict a schematic blow molding system 300 which illustrates deforming a polymer tube with blow molding. In some embodiments, a polymer tube for use in manufacturing stent can have a diameter of 1-3 mm. However, the present invention is applicable to polymer tubes less than 1 mm or greater than 3 mm. The wall thickness of the polymer tube can be 0.03-0.06 mm, however, the present invention is application to tubes with a wall thickness less than 0.03 mm and greater than 0.06 mm.

FIG. 3A depicts an axial cross-section of a polymer tube 301 with an undeformed outside diameter 305 positioned within a mold 310. Mold 310 limits the radial deformation of polymer tube 301 to a diameter 315, the inside diameter of mold 310. Polymer tube 301 may be closed at a distal end 320. Distal end 320 may be open in subsequent manufacturing steps. A fluid may be conveyed, as indicated by an arrow 325, into an open proximal end 321 of polymer tube 301 to increase an internal pressure within tube 301 to radially deform tube 301. A tensile force can be applied at proximal end 321, a distal end 320, or both.

Polymer tube 301 is heated by a nozzle 330 with fluid ports that direct a heated fluid at two circumferential locations of tube 310, as shown by arrows 335 and 340. FIG. 3B depicts a radial cross-section showing tube 301, mold 310, and nozzle 330 having structural members 360. Additional fluid ports can be positioned at other circumferential locations of tube 310. The heated fluid flows around tube 301, as shown by arrows 355, to heat mold 310 and tube 301 to a temperature above ambient temperature.

Nozzle 330 translates along the longitudinal axis of tube 310 as shown by arrows 365 and 367. As nozzle 330 translates along the axis of mold 310, tube 301 radially deforms. The increase in temperature of tube 301 and the increased pressure cause deformation of tube 301, as depicted in FIG. 3C.

FIG. 3C depicts system 300 with a deforming section 372 and deformed section 370 of tube 301. Section 372 deforms radially as shown by an arrow 380. Deformed section 370 has an outside diameter the same as the inside diameter of mold 310.

Processing parameters of the above-described deformation process include, but are not limited to, the deformation temperature, deformation pressure (or force), nozzle translation rate, heat setting temperature, and the time of heat setting. It is expected that the deformation rate depends at least upon the deformation pressure, deformation temperature, and heat source or nozzle translation rate. The deformation rate has both a radial component in the radial direction and an axial component corresponding to the propagation rate of the radial deformation along the axis of the tube. The deformation in the radial direction is shown by arrow 380 in FIG. 3C and the axial component is shown by an arrow 382 in FIG. 3C. It is expected that the radial deformation rate has a greater dependence on the deformation pressure and the axial component has a greater dependence on the translation rate of the heat source along the axis of the tube. Since deformation of a polymer is a time dependent process, it is expected that the deformation rate will also affect the morphology and structure of the deformed polymer. The morphology and consequently the mechanical properties of the deformed tube are expected to depend upon the processing parameters.

Embodiments of the present invention include determining or optimizing processing parameters of a blow molding process of a polymer tube. In such embodiments, the processing parameters are determined or optimized to achieve or provide desired mechanical properties of a stent fabricated from the blow molded or deformed tube. In some embodiments, the processing parameters can be determined or optimized to obtain a selected morphology of the polymer of the deformed tube that provides the desired mechanical properties. Additionally, in such embodiments, the processing parameters include, but are not limited to, the deformation temperature, deformation pressure, and nozzle speed. Further embodiments of the present invention include controlling, adjusting, or modifying processing parameters of a blow molding process of a polymer tube that provide the desired mechanical properties. In these embodiments, a stent may then be fabricated from the blow molded tube.

In some embodiments, the processing parameters that provide desired mechanical properties can be determined or optimized by blow molding two or more tubes. One or more the processing parameters can be varied so that two or more tubes are blow molded with at least one different processing parameter. Stents can then be fabricated from the tubes and the mechanical properties and performance determined for the stents using known testing techniques. For example, the radial strength and modulus can be determined. The toughness and fracture resistance can be evaluated by examining the fracture and breaking of struts when the stents are expanded to a deployment diameter or greater than a deployment diameter. Additionally, the morphology (e.g., crystallinity, molecular orientation of polymer chains, and crystal size) of the tubes can be determined by known testing techniques, as discussed in examples below.

Furthermore, the desired mechanical properties can include high radial strength, high toughness, high modulus, and low recoil. A polymer stent fabricated from the polymer tube can have a high resistance to failure upon expansion of the stent. The high resistance to failure can be demonstrated by few or no cracks in struts of a stent or no broken struts upon expansion of the stent to a deployment diameter. In such embodiments, the processing parameters can be modified to change the morphological characteristics, such as crystallinity, molecular orientation of polymer chains, and crystal size.

In certain embodiments, the axial propagation rate, the radial deformation rate, the deformation temperature, or any combination thereof can be optimized and controlled to provide selected or desired mechanical properties of a stent such as selected fracture resistance. In such embodiments, the axial propagation rate or the radial deformation rate can be controlled or adjusted by the deformation pressure, heat source translation rate, the deformation pressure, or a combination thereof.

Figure 4:
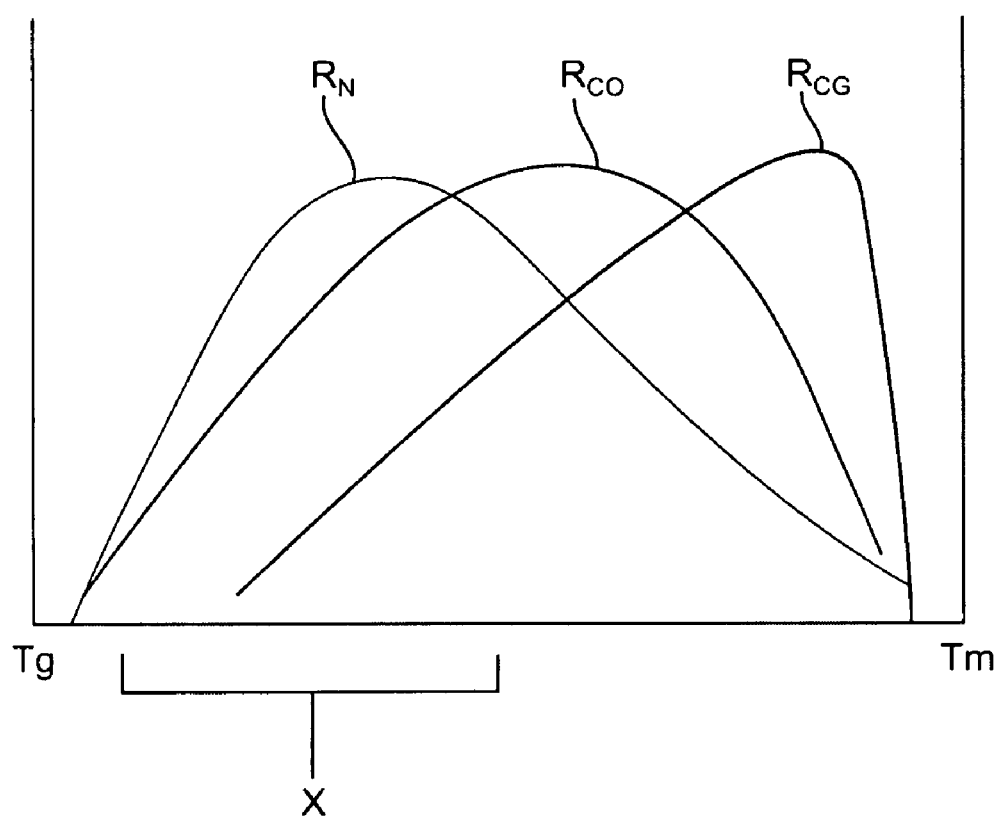
FIG. 4 depicts a schematic plot of the crystal nucleation rate and the crystal growth rate, and the overall rate of crystallization.

The temperature of the deformation process can be used to control the degree of crystallinity and the size of the crystalline domains. In general, crystallization tends to occur in a polymer at temperatures between Tg and Tm of the polymer. The rate of crystallization in this range varies with temperature. FIG. 4 depicts a schematic plot of the crystal nucleation rate ($R_N$), the crystal growth rate ($R_{CG}$), and the overall rate of crystallization ($R_{CO}$). The crystal nucleation rate is the growth rate of new crystals and the crystal growth rate is the rate of growth of formed crystals. The overall rate of crystallization is the sum of curves $R_N$ and $R_{CG}$.

In certain embodiments, the temperature of the tube during deformation can be controlled to have a crystallization rate that provides a selected degree of crystallization and crystal size distribution. In some embodiments, the temperature can be in a range in which the crystal nucleation rate is larger than the crystal growth rate. For example, as shown in FIG. 4, the temperature can be in a range as shown by "X". In such embodiments, the temperature can be in a range at which the crystal nucleation rate is relatively high and the crystal growth rate is relatively low. For example, the temperature can be in a range where the ratio of the crystal nucleation rate to crystal growth rate is 2, 5, 10, 50, 100, or greater than 100. In exemplary embodiments, the temperature can be from about Tg to about 0.6(Tm−Tg)+Tg or from about Tg to about 0.9(Tm−Tg)+Tg.

Under these conditions, the resulting polymer can have a relatively large number of crystalline domains that are relatively small. As the size of the crystalline domains decreases along with an increase in the number of domains, the fracture toughness of the polymer can be increased reducing or minimizing brittle behavior. By deforming and the polymer tube as described, the size of the crystals can range from less than about 15, less than about 10, less than about 6, less than about 2, or less than about 1 micron.

Figure 5:
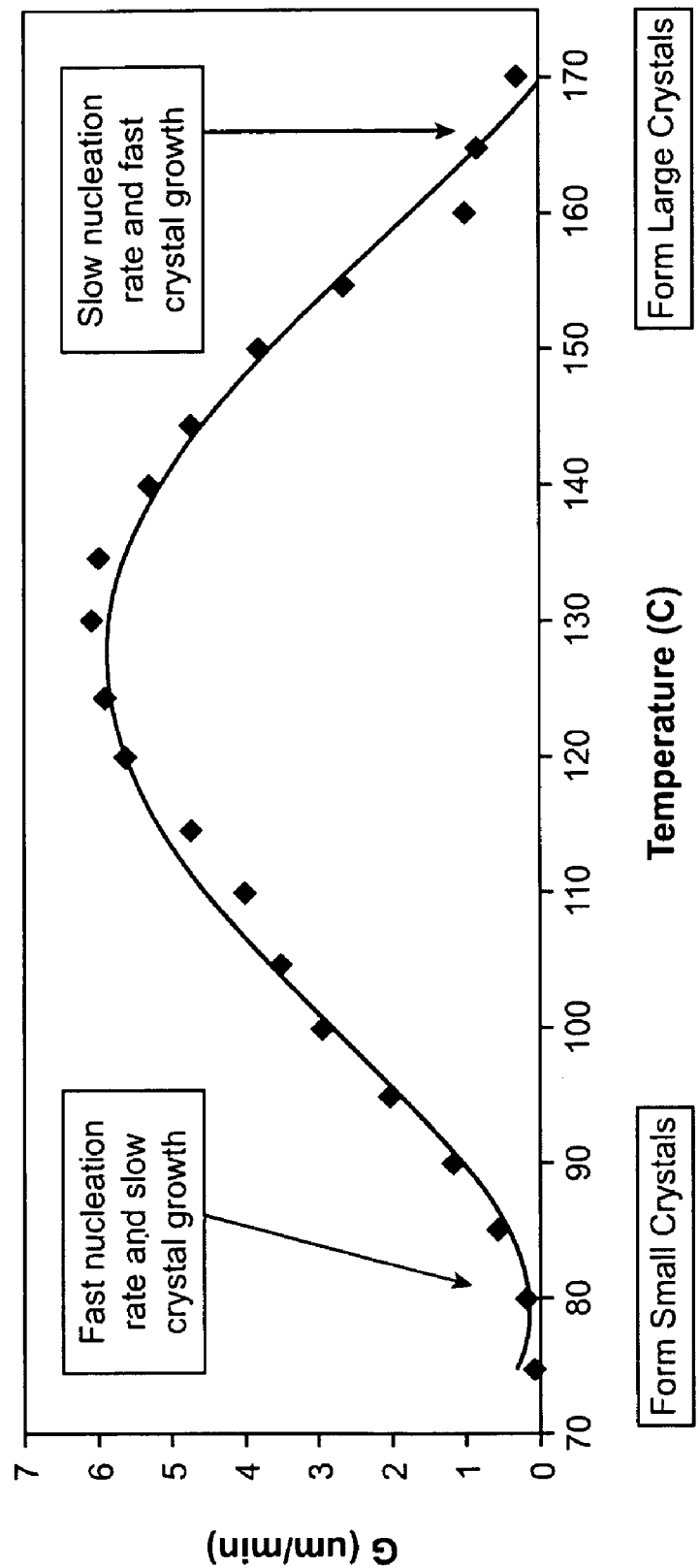
FIG. 5 depicts experimental results for the $R_{CG}$ of PLLA.

FIG. 5 depicts experimental results for the $R_{CG}$ of PLLA. (Eur. Polymer Journal, 2005) At lower temperatures, there is fast nucleation rate and slow crystal growth rate and at higher temperatures, there is slow nucleation rate and fast crystal growth.

In certain embodiments, the processing parameters can be modified to obtain a morphology corresponding to an amorphous structure having relatively small crystalline domains with polymer chains having a high degree of orientation. The size of the crystalline domains can be minimized by adjusting a temperature in the range X shown in FIG. 4. A pressure and nozzle speed can also be adjusted to obtain the desired mechanical properties. As shown in the examples below, the deformation pressure and nozzle speed can be adjusted to increase the strength and toughness of the deformed polymer tube.

Polymers can be biostable, bioabsorbable, biodegradable or bioerodible. Biostable refers to polymers that are not biodegradable. The terms biodegradable, bioabsorbable, and bioerodible are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Example 1

The following example describes the adjusting or optimizing of morphology and mechanical properties of expanded PLLA tubes. A commercially available balloon blower or expander was used for radially expanding the polymer tubes. The expander was modified to allow change in morphology at different process conditions. The modified expander includes a displacement control function. The displacement control function allows fabrication of samples of expanded tubing with different mechanical properties from the same source or lot of extruded tubing.

The effect of three process parameters on the morphology of the polymer tube and mechanical properties of stents was studied. These parameters include the deformation temperature, deformation pressure, and nozzle speed. Tubes were deformed using two different values for each parameter to examine influence of the parameters and different combinations of values of parameters on the properties of the tubes and stents. Deformation runs using three combinations of these values were performed to determine optimal values and combinations for the parameter values.

Table 1 lists the values of the deformation temperature and the relative deformation pressure and speed. High and low temperature and pressures and a slow and fast nozzle speeds were used. The different parameter values are expected to provide different crystallization rates, radial deformation rates, and axial deformation rates. The high temperature provides a higher crystallization rate compared to the low temperature. The high pressure provides a higher radial deformation rate compared to the low pressure. The fast nozzle speed provides a higher axial deformation rate than the slow nozzle speed.

TABLE 1

Values of deformation temperature and deformation pressure

| Temp (° F.) | Relative Pressure | Relative Speed |
|---|---|---|
| 200 | low | slow |
| 300 | high | fast |

Tubes were deformed using three different combinations or options of the parameter values shown in Table 1. Table 2 lists the three combinations of the processing parameter values.

TABLE 2

Combinations or options of processing parameters.

| Option | Temp | Pressure | Speed |
|---|---|---|---|
| 1 | High | High | Fast |
| 2 | Low | High | Slow |
| 3 | Low | Low | Slow |

Figure 6:
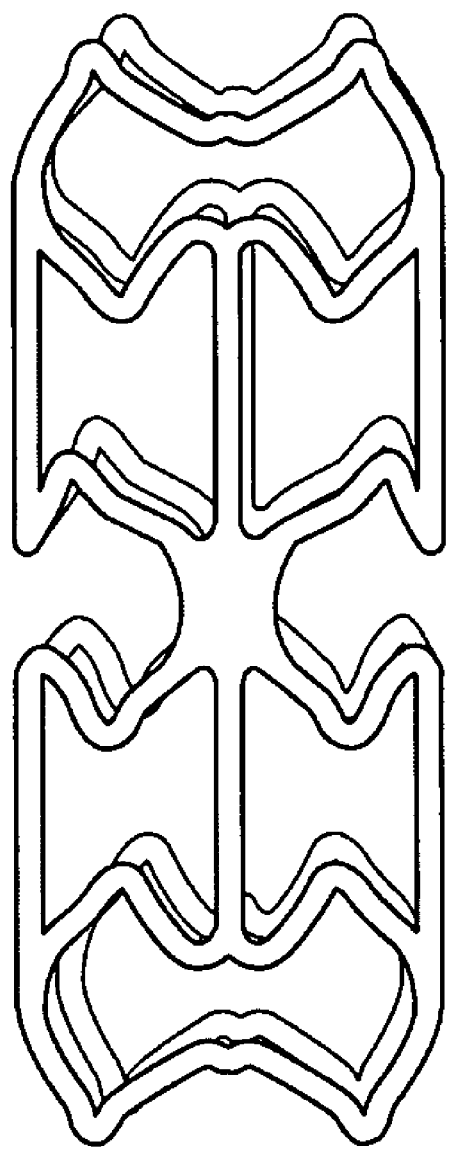
FIG. 6 illustrates the stent pattern of the stent used in the testing.

Polymer tubes were deformed at the processing conditions for each option. The tubes were then made into stents for mechanical testing. FIG. 6 illustrates the stent pattern of the stent used in the testing. The stents were designed for 3.0 mm deployment. Stents were aged by heat-setting in an oven at 40° C. for 16 hours. Stent were deployed to 3.5 mm and 4.0 mm in order to induce failure during testing. This testing technique allows the observation of stent failure early at extreme conditions. The stents were fabricated from tubes with the same dimension of expanded tubing, with different processing conditions used to expand the tubes.

Figure 7:
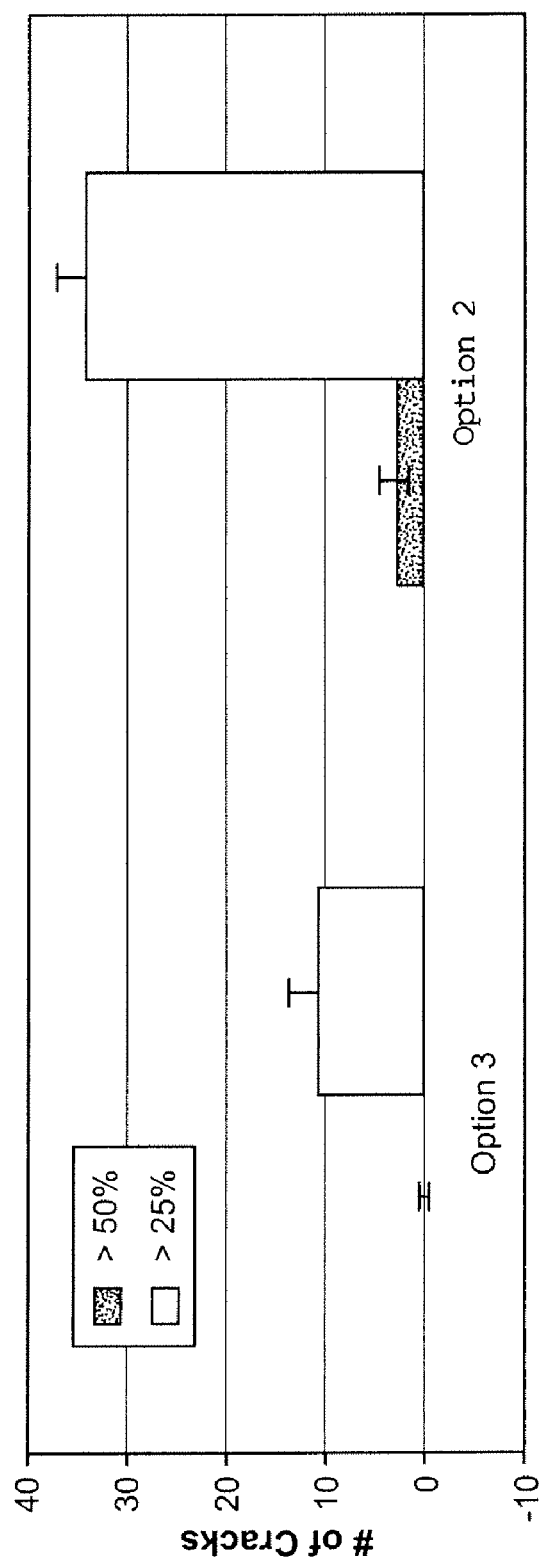
FIG. 7 is a graph showing the number of cracks observed in stents made from tubes with different expansion process parameters.

The toughness of the stents were assessed through comparison of the number of cracks observed in the stent samples at zero time point when deployed at diameters of 3.5 mm and 4 mm. FIG. 7 is a graph showing the number of cracks observed in stents made from tubes processed using options 2 and 3. Two different crack size ranges were determined: ">25%" refers to cracks greater than 25% of the strut width. ">50%" refers to cracks greater than 50% of the strut width. As shown in FIG. 7, the number of cracks for option 3 stents for each crack size is less than the corresponding crack size for option 2 stents.

Table 3 shows crack data for stents made from tubes processed with option 1 and option 2 parameters. The results for four stents at each option are shown. Table shows that for stents deployed to 3.5 mm, the cumulative number of cracks for option 2 stents at each crack number range is less than for option 1 stents. No broken struts were observed at 3.5 mm for any of the stents tested. The option 1 stents had more broken struts at 4 mm deployment than the option 2 stents.

TABLE 3

Crack counts for stents made from tubes processed with option 1 (300° F.) and option 2 (200° F.) processing parameters.

| Stent | Expansion Temp (° F.) | Crack > 25% at 3.5 mm | Crack > 50% at 3.5 mm | Broken Strut at 3.5 mm | Broken Strut at 4.0 mm |
|---|---|---|---|---|---|
| B-1 | 200 | 0 | 0 | 0 | 0 |
| B-2 | 200 | 2 | 0 | 0 | 2 |
| B-3 | 200 | 0 | 0 | 0 | 0 |
| B-4 | 200 | 2 | 0 | 0 | 0 |
| C-1 | 300 | 4 | 2 | 0 | 10 |
| C-2 | 300 | 4 | 1 | 0 | 7 |
| C-3 | 300 | 2 | 1 | 0 | 4 |
| C-4 | 300 | 3 | 1 | 0 | 5 |

Table 4 summarizes the comparison of the three processing options shown in Table 2. As shown, option 3 provides the best mechanical performance which is demonstrated in FIG. 7 and Table 3. The appearance of the deformed tubes is also affected by processing conditions. Option 3 parameters result in a tube having a clear appearance. It is believed that option 3 provides the best mechanical performance in part because the lower temperature results in the formation of a greater number of smaller crystalline domains. Additionally, option 3 is better because the slower deformation rate facilitates the development of an oriented molecular structure with reduced internal stresses.

TABLE 4

Summary of results for options 1, 2, and 3.

| Option | Temp | Pressure | Speed | Appearance | Stent Performance | Morphology Development |
|---|---|---|---|---|---|---|
| 1 | High | High | Fast | Clear | Worse | Faster crystallization temp. Faster deformation Higher crystallinity, lower amorphous orientation |
| 2 | Low | High | Slow | Hazy | Better | Faster deformation in radial direction Lower crystallization rate |
| 3 | Low | Low | Slow | Clear | Best | Slower deformation rate Lower crystallization rate |

Example 2

Table 5 depicts desirable processing conditions for expanding a tube that provide good stent performance for three stent materials. The first material is 100% PLLA. The second is a PLLA/elastomeric polymer blend that includes PLLA with a dispersed elastomeric block copolymer to increase toughness. The elastomeric copolymer is (CL-co-GA)-b-PLLA. The (CL-co-GA) blocks form a dispersed elastomeric phase and the PLLA block increases adhesion between the PLLA matrix and the elastomeric phase. The third material is the polymer blend with dispersed bioceramic nano-particles.

TABLE 5

Desirable tube expansion parameters for three stent materials.

| Run | Temp (° F.) | Pressure (psi) | Speed (mm/s) | Appearance | Stent Performance | Polymer |
|---|---|---|---|---|---|---|
| 1 | 200 ± 20 | 130 ± 20 | 0.6 | Clear | Good | 100% PLLA |
| 2 | 190 ± 10 | 120 ± 20 | 0.6 | Hazy | Good | PLLA/Elastomeric copolymer Blend |
| 3 | 190 ± 10 | 120 ± 20 | 0.6 | Hazy | Good | PLLA/Elastomeric copolymer/nano-particles |

Example 3

The following example describes a study on the effect of deformation temperature on morphology for expanded PLLA tubes. Table 6 lists the four samples that were studied. Stent samples 1 and 4 were made from tubes expanded at 200° F. and samples 2 and 3 were made from tubes expanded at 300° F.

TABLE 6

Tube dimension, expansion ratio and appearance of stent samples.

| | Before Expansion | | After Expansion | | | |
|---|---|---|---|---|---|---|
| | ID | OD | ID | OD | RE % | Appearance |
| #1 | 0.017 | 0.0565 | 0.073 | 0.0845 | 300% | Transparent |
| #2 | 0.016 | 0.06 | 0.082 | 0.094 | 412% | Turbid |
| #3 | 0.014 | 0.06 | 0.082 | 0.094 | 486% | Turbid |
| #4 | 0.024 | 0.074 | 0.125 | 0.137 | 421% | Turbid |

Differential scanning calorimetry (DSC) was used to determine the crystallinity of each of the samples. Table 7 lists the enthalpy of crystallization, enthalpy of melting, and % crystallinity for each sample. As expected, the % crystallinity is lower for samples 1 and 4 than for samples 2 and 3 due the higher crystal growth rate at the higher temperature.

TABLE 7

DSC results for expanded tubing.

| | $\nabla Hc$ (J/g) | $\nabla Hm$ (J/g) | $Xc$ (%) |
|---|---|---|---|
| #1 | 3.332 | 51.17 | 51.4% |
| #2 | 1.285 | 49.87 | 52.2% |
| #3 | 0.8725 | 49.85 | 52.7% |
| #4 | 1.576 | 48.19 | 50.1% |

Wide angle x-ray scattering (WAXS) was used to determine the crystal size in the expanded tubes. The tube samples were scanned both horizontally along the tube axis and vertically perpendicular to the tube axis. Table 8 shows the results of the WAXS for the four stent samples. As expected, samples 1 and 4 had smaller crystal sizes than samples 2 and 3 since the crystal growth rate is smaller at the lower temperature.

TABLE 8

Crystal Size of samples from X-ray

| Sample | | Linewidth | 2θ | Crystal size/nm |
|---|---|---|---|---|
| #1 | H | 0.83261 | 16.456 | 9.95 |
| | V | 0.7590 | 16.414 | 10.9 |
| #2 | H | 0.58275 | 16.457 | 14.2 |
| | V | 0.49191 | 16.477 | 16.8 |
| #3 | H | 0.60212 | 16.509 | 13.8 |
| | V | 0.56963 | 16.546 | 14.5 |
| #4 | H | 0.95572 | 16.427 | 8.67 |
| | V | 0.73321 | 16.478 | 11.3 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a stent comprising:
   radially deforming a polymer tube for use in fabrication of a stent from the deformed tube, wherein the radial deformation propagates along the tube axis as the tube is heated along the axis, the polymer tube having an internal tube pressure higher than ambient translating a heat source along an axis of the pressurized polymer tube to heat the tube to the deformation temperature, wherein the heat source is translated at a rate of 0.5 to 0.7 mm/s;
   controlling a temperature of the deforming polymer tube to provide a selected fracture toughness of the stent fabricated from the tube, wherein the temperature is controlled to provide a morphology of the polymer tube that provides the selected fracture toughness, and wherein the temperature is in a range in which a polymer crystal nucleation rate is larger than a polymer crystal growth rate; and
   fabricating the stent from the deformed tube.

2. The method of claim 1, wherein the selected fracture toughness of the stent comprises a fracture toughness of the stent when radially expanded to a deployment diameter.

3. The method of claim 1, wherein the temperature is controlled to provide a morphology of the deformed polymer tube comprising an amorphous matrix including dispersed crystalline regions.

4. The method of claim 3, wherein the crystalline regions have a size less than about 15 microns.

5. The method of claim 3, wherein the crystalline regions have a size less than about ten microns.

6. The method of claim 1, wherein the temperature is controlled to provide a morphology of the deformed polymer tube comprising less than about 40% crystallinity.

7. The method of claim 1, wherein the temperature is controlled to be from about Tg to about 0.6(Tm−Tg)+Tg, where Tg is the glass transition temperature of the polymer and Tm is the melting temperature of the polymer.

8. The method of claim 1, wherein the polymer tube is made of poly(L-lactide) and the temperature is controlled to be in the range 180° F. to 220° F.

9. A method for fabricating a stent comprising:
   increasing an internal pressure of a tube to a deformation pressure;
   translating a heat source along an axis of the pressurized polymer tube to heat the tube to a deformation temperature, wherein the heat source is translated at a rate of 0.5 to 0.7 mm/s;
   allowing the tube to radially expand as the heat source translates along the axis of the polymer tube, wherein the heating of the tube and the increase in pressure allow the tube to radially expand; and
   controlling the deformation temperature to provide a selected fracture toughness to a stent fabricated from the tube wherein the deformation temperature is controlled to provide a morphology of the deformed polymer tube comprising about 50% crystallinity; and
   fabricating the stent from the expanded tube.

10. The method of claim 9, wherein the selected fracture toughness of the stent comprises no cracks in stent struts greater than 50% of the strut width or no broken struts when radially expanded to a deployment diameter.

11. The method of claim 9, wherein the temperature is controlled to provide a morphology of the deformed polymer tube comprising an amorphous matrix including dispersed crystalline regions.

12. The method of claim 9, wherein the deformation temperature is controlled to be from about Tg to about 0.6(Tm−Tg)+Tg.

13. The method of claim 9, wherein the polymer tube is made of poly(L-lactide) and the deformation temperature is controlled to be in the range 180° F. to 220° F.

14. A method for fabricating a stent comprising:
   determining a deformation temperature of a radial deformation process of a tube to provide a selected fracture toughness of a stent fabricated from the tube, wherein the temperature is controlled to provide a morphology of the polymer tube that provides the selected fracture toughness and wherein the temperature is in a range in which a polymer crystal nucleation rate is larger than a polymer crystal growth rate, the radial deformation process comprising:
   increasing an internal pressure of a tube to a deformation pressure;
   translating a heat source along an axis of the pressurized polymer tube to heat the tube to the deformation temperature, wherein the heat source is translated at a rate of 0.5 to 0.7 mm/s;
   allowing the tube to radially expand as the heat source translates along the axis of the polymer tube, wherein the heating of the tube and the increase in pressure allow the tube to radially expand; and
   fabricating the stent from the expanded tube.

15. The method of claim 14, wherein the temperature is controlled to provide a morphology of the deformed polymer tube comprising less than about 40% crystallinity.

16. The method of claim 14,
   wherein the tube is a poly(L-lactide) tube,
   the internal pressure is increased to between 120 psi and 130 psi, and
   the heat source heats the tube to between 180° F. and 220° F.

17. The method of claim 16, wherein prior to expansion a diameter of the tube is 1-3 mm.

18. A method for fabricating a stent comprising:
   increasing an internal pressure of a tube to a deformation pressure;
   translating a heat source along an axis of the pressurized polymer tube to heat the tube to a deformation temperature;
   allowing the tube to radially expand as the heat source translates along the axis of the polymer tube, wherein the heating of the tube and the increase in pressure allow the tube to radially expand; and
   controlling the deformation temperature, wherein the heat source is translated at a rate of 0.5 to 0.7 mm/s to provide a selected fracture toughness to a stent fabricated from the tube wherein the temperature is controlled to provide a morphology of the deformed polymer tube comprising an amorphous matrix including dispersed crystalline regions and wherein the crystalline regions have a size less than about ten microns; and
   fabricating the stent from the expanded tube.

19. A method for fabricating a stent comprising:
   increasing an internal pressure of a tube to a deformation pressure;
   translating a heat source along an axis of the pressurized polymer tube to heat the tube to a deformation temperature, wherein the heat source is translated at a rate of 0.5 to 0.7 mm/s;
   allowing the tube to radially expand as the heat source translates along the axis of the polymer tube, wherein the heating of the tube and the increase in pressure allow the tube to radially expand; and controlling the deformation temperature to provide a selected fracture toughness to a stent fabricated from the tube wherein the temperature is controlled to provide a morphology of the deformed polymer tube comprising an amorphous matrix including dispersed crystalline regions and wherein the crystalline regions have a size less than about 15 microns; and fabricating the stent from the expanded tube.

* * * * *

UNITED STATES PATENT AND TRADEMARK OFFICE
CERTIFICATE OF CORRECTION

PATENT NO. : 8,268,228 B2  
APPLICATION NO. : 12/001777  
DATED : September 18, 2012  
INVENTOR(S) : Huang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Second Day of September, 2014

Michelle K. Lee
*Deputy Director of the United States Patent and Trademark Office*